United States Patent [19]

Satoh

[11] Patent Number: 4,731,336

[45] Date of Patent: Mar. 15, 1988

[54] IMMUNOASSAY FOR COMPLEMENT FRAGMENTS

[75] Inventor: Paul S. Satoh, Portage, Mich.

[73] Assignee: Amersham International plc, Buckinghamshire, England

[21] Appl. No.: 928,608

[22] Filed: Nov. 3, 1986

Related U.S. Application Data

[63] Continuation of Ser. No. 806,111, Dec. 4, 1985, abandoned, which is a continuation of Ser. No. 754,661, Jul. 11, 1985, abandoned, which is a continuation of Ser. No. 518,603, Jul. 29, 1983, abandoned, which is a continuation-in-part of Ser. No. 388,068, Jun. 14, 1982, abandoned.

[51] Int. Cl.$^4$ ................. G01N 33/564; G01N 33/536
[52] U.S. Cl. ..................................... 436/506; 436/536; 436/538; 436/539; 436/540; 436/542; 436/809; 436/821; 436/825
[58] Field of Search ............... 436/506, 507, 536, 538, 436/540, 542, 539, 543–546, 804, 808–810, 811, 815, 821, 822, 824, 825, 826; 435/7, 18, 23, 24, 810

[56] References Cited

U.S. PATENT DOCUMENTS 3,607,857 9/1971 Nelson ................................. 260/112
3,745,155 7/1973 Dahlgren ......................... 260/112 B
3,903,254 9/1975 Dahlgren ............................... 424/12

OTHER PUBLICATIONS

T. E. Hugli and D. E. Chenoweth, "Biologically Active Peptides of Complement: Techniques & Significance of C3a and C5a Measurements", Immunoassays: Clinical Lab. Techniques for the 1980's, A. R. Liss, Inc., New York, 1980, pp. 443–460.
M. Stastny and J. Horeisi, "The Interaction of Acridine Dyes with Blood Plasma Proteins", Clin. Chim. Acta, 6, 1961, pp. 782–793.
Hood, L. E., et al, Immunology, p. 49.
Benjamin Cummings Co., Menlo Park, Calif. (1978).
Baumgarten, A., Immunology, CRC Handbook Series Section F, pp. 89–116, CRC Press (1979).
Satoh, Paul S., Biotechnique, vol. 1(2), pp. 90–95 (1983).

*Primary Examiner*—Margaret Moskowitz
*Attorney, Agent, or Firm*—Wenderoth, Lind & Ponack

[57] ABSTRACT

A method for assaying complement fragment $C_3a$, $C_4a$ or $C_5a$ or the des-Arg derivative thereof in a biological sample which comprises combining equal volumes of the biological sample and a solution of 0.8 to 1.6% of an acridine derivative selected from the group consisting of acrinol, acriflavine, acriflavine hydrochloride, and aminacrine, incubating the mixture for about one minute to 2 hour at about 25° C., recovering the supernatant from the resultant precipitate, incubating the supernatant with a known amount of a labeled complement fragment selected from $C_3a$, $C_4a$ or $C_5a$ or the des-Arg derivative thereof and a known amount of antibody which recognizes said complement fragment or des-Arg derivative thereof, separating the free labeled complement fragment from the bound labeled complement fragment, measuring the amount of labeled complement fragment in either the free or antibody bound complement component, and determining the concentration of complement fragment or the des-Arg derivative thereof in the biological sample by comparison to a standard curve and a mercantil kit useful in performing said method.

15 Claims, No Drawings

IMMUNOASSAY FOR COMPLEMENT FRAGMENTS

CROSS REFERENCE TO RELATED APPLICATION

This application is a continuation of application Ser. No. 06/806,111, filed Dec. 4, 1985, now abondoned, which is a continuation of application Ser. No. 06/754,661, filed July 11, 1985, now abandoned, which is a continuation of application Ser. No. 06/518,603, filed July 29, 1983, now abandoned, which is a continuation-in-part of application Ser. No. 06/388,068, filed June 14, 1982, now abandoned.

FIELD OF INVENTION

The present invention provides an improved method for assaying complement fragments $C_3a$, $C_4a$ and $C_5a$ or the des-Arg derivatives thereof and a mercantile kit useful in performing said immunoassay.

BACKGROUND OF THE INVENTION

The complement system of humans and other mammals involves more than 20 components which participate in an orderly sequence of reactions resulting in complement activation. Numerous studies indicate that the complement system is a fundamental element of normal host defense mechanisms. As a consequence, complement activation is commonly associated with a variety of pathological states such as certain malignancies, myocardial infarction, systemic lupus erythematosis, and adult respiratory distress syndrome. Because of these correlations clinical laboratory methods that detect complement activation are useful in diagnosing certain disease conditions.

Complement activation can occur by either of two primary modes known as the "classical" pathway and the "alternative" pathway, respectively. These different pathways are generally distinguished according to the process which initiates complement activation. Activation via the classical pathway is usually associated with an immunologic stimulus whereas activation via the alternative pathway is most commonly associated with non-immunologic stimuli. Regardless of the initiating stimulus both pathways converge, followed by the conversion of the $C_3$ component of complement into its $C_3a$ and $C_3b$ fragments. This cleavage of $C_3$ into its subcomponents its considered to be one of the significant events signalling activation of the alternate complement cascade. Following the conversion of $C_3$, a $C_5$ convertase enzyme complex is formed. This enzyme cleaves the $C_5$ component to yield the fragments $C_5a$ and $C_5b$. Complement activation by the classical pathway mechanism is uniquely characterized by the fact that this route leads to the conversion of the $C_4$ component to its fragments $C_4a$ and $C_4b$.

The physicochemical and physiological properties of the cleavage products $C_3a$, $C_4a$ and $C_5a$, termed anaphylatoxins are well known. Each is a potent bioactive polypeptide and plays a key role as a mediator of acute inflammatory processes. Among these three anaphylatoxins $C_5a$ alone is uniquely characterized by its ability to interact with white blood cells. Both $C_3a$ and $C_4a$ are rendered inactive in vivo by conversion of their respective des arginine derivatives ($C_3a_{des\ Arg}$ or $C_3a_i$, $C_4a_{des\ Arg}$ or $C_4a_i$) by a serum carboxypeptidase. Human $C_5a$, on the other hand, is converted to $C_5a_{des\ Arg}$ by this serum carboxypeptidase only after all available white blood cell binding sites for $C_5a$ have been saturated.

Conversion of the human complement components $C_3$ and $C_5$ to yield their respective anaphylatoxin products has been implicated in certain naturally occurring pathologic states including: autoimmune disorders such as systemic lupus erythematosis, rheumatoid arthritis, malignancy, myocardial infarction, Purtscher's retinopathy, and adult respiratory distress syndrome. In addition, increased circulating levels of $C_3a$ and $C_5a$ have been detected in certain conditions associated with iatrogenic complement activation such as: cardiopulmonary bypass surgery, renal dialysis, and nylon fiber leukaphoresis. Elevated levels of $C_4a$ anaphylatoxin are commonly associated with the autoimmune disorders mentioned above. Therefore, the ability to quantitatively measure the circulating levels of these anaphylatoxins or their des-Arg derivatives is of great utility in diagnosing a variety of important pathological conditions. Additionally, the ability to measure levels of $C_4a$ or $C_4a_{des\ Arg}$ enables one to determine the pathway by which complement activation occurs. This facility enables one not only to determine the precise mechanism of complement activation but also whether a patient's natural immunological defense mechanisms are functional.

Until the development of the radioimmunoassay (RIA) method of Tony E. Hugli and Dennis E. Chenoweth reported in "Immunoassays: Clinical Laboratory Techniques for the 1980s," 443–460, Alan R. Liss, Inc., New York, NY (1980), measurement of the anaphylatoxins $C_3a$, $C_4a$ and $C_5a$ or their des-Arg derivatives had only been achieved when the levels of these factors were relatively elevated, for example, when the disease process had reached an advanced stage. The RIA techniques of Hugli and Chenoweth permit quantitative measurement of trace amounts of the anaphylatoxins or their des-Arg derivatives and hence provide a sensitive diagnostic tool. However, the means known heretofore for measuring these factors have been frought with a significant problem associated with the requirement that the $C_3$, $C_4$ and $C_5$ plasma precursors of the anaphylatoxins must be removed from the biological fluid to be tested. This stringent requirement is predicated on the observation that the antibodies raised to the anaphylatoxins possess a significant cross-reactivity with their respective plasma precursor as $C_3a$, $C_4a$ or $C_5a$ is a part of the parent molecule $C_3$, $C_4$ and $C_5$, respectively. Because of this unavoidable cross-reactivity it is imperative that the precursor which exists in relatively high concentrations in serum and plasma be completely removed to avoid detecting artifactually elevated levels of the anaphylatoxins which are normally present in only trace amounts. Prior known methods of separating the anaphylatoxins from their plasma precursors involves diluting the plasms with sodium chloride and acidifying with hydrochloric acid and subsequently neutralizing the recovered serum sample. See Hugli and Chenoweth cited above. The present invention provides a novel and simplified means of quantitatively removing the plasma precursor of the anaphylatoxin from the biological samples yet simultaneously permitting a quantitative recovery of the low molecular weight anaphylatoxins, $C_3a$, $C_4a$ and $C_5a$ or the des-Arg derivatives thereof.

SUMMARY OF INVENTION

The present invention provides a novel method for removing substantially all traces of complement precursors or components $C_3$, $C_4$ and $C_5$ from samples of biological fluids and recovering from said fluids complement fragments $C_{3a}$, $C_{4a}$ and $C_{5a}$ or the des-Arg derivatives thereof without interfering with the immunogenicity of said fragments which comprises combining equal volumes of the biological fluid sample and a buffered solution of 0.8 to 1.6% of an acridine derivative selected from the group consisting of acrinol, acriflavine, acriflavine hydrochloride and aminacrine, incubating the mixture for from one minute to 2 hours at about 25° C. and recovering the supernatant from the resultant precipitate.

The present invention also provides a novel and improved method for quantitatively measuring complement fragments $C_{3a}$, $C_{4a}$ or $C_{5a}$ or the des-Arg derivatives thereof in a biological sample which comprises combining equal volumes of the biological sample and 0.8 to 1.6% of an acridine derivative selected from the group consisting of acrinol, acriflavine, acriflavine hydrochloric and aminacrine, incubating the mixture for from one minute to 2 hours at about 25° C., recovering the supernatant from the resultant precipitate, and incubating the supernatant with a known amount of a labeled complement fragment selected from $C_{3a}$, $C_{4a}$ or $C_{5a}$ or the des-Arg derivative thereof and a known amount of an antibody which recognizes said labeled complement fragment or des-Arg derivative thereof, separating the free labeled complement fragment from the bound labeled complement fragment, measuring the amount of labeled complement fragment in either the free or antibody bound complement component, and determining the concentration of complement fragment in the biological sample by reference to a standard curve.

The present invention also provides a novel kit wherein the component parts are assembled for use in assaying samples of biological fluids for complement fragments $C_{3a}$, $C_{4a}$ and $C_{5a}$ or the des-Arg derivatives thereof which comprises a first container having therein a buffered solution of 0.8 to 1.6% solution of an acridine derivative selected from the group consisting of acrinol, acriflavine, acriflavine hydrochloride and aminacrine; a second container having therein a labeled reagent selected from labeled complement fragments $C_{3a}$, $C_{4a}$ or $C_{5a}$ or the des-Arg derivatives thereof; and a third container having therein an antibody reagent selected from antibody which recognizes complement fragments $C_{3a}$, $C_{4a}$ or $C_{5a}$ or the des-Arg derivatives thereof.

DETAILED DESCRIPTION OF INVENTION

As used herein acrinol is taken to mean 2-ethoxy-6,9-diaminoacridine or the lactate monohydrade salt thereof; acriflavine means a mixture of 3,6-diamino-10-methylacridinium chloride and 3,6-diaminoacridine containing when dried at 105° C. for two hours not less than 13.3% and not more than 15.8% of Cl; acriflavine hydrochloride means a mixture of the hydrochlorides of 3,6-diamino-10-methylacridinium chloride and 3,6-diaminoacridine containing when dried for one hour at 105° C. not less than 23% and not more than 23.5% of Cl; and aminacrine means 5-aminoacridine.

In practicing the present invention the sample of biological fluid can be any bodily fluid such as, for example, serum, plasma, urine or cerebrospinal fluid. When the biological fluid employed is plasma or cerebrospinal fluid EDTA is added thereto.

Equal volumes of the biological fluid and 0.8 to 1.6% of the acridine derivative are combined for a final concentration of 0.4 to 0.8% of said acridine derivative. The preferred final concentration of acridine derivative is 0.6%. The acridine derivative-protein complex is buffered to a pH of about 7.4. Any buffer which does not contain chloride ions is suitable, for example, carbonate buffers, phosphate, buffers, or HEPES (N-2-hydroxyethylpiperazineethane sulfonic acid) may be employed. Preferably the molarity of the buffer is between 0.05 to 0.1M with a pH of from 6.8 to 7.8. The preferred buffer for use in practicing the present invention is 0.05M phosphate buffer, pH 7.4.

Once the biological fluid and acridine derivative are combined a precipitate forms almost immediately. However, the complex preferably should be permitted to incubate for at least about 20 minutes to effect maximum separation of the complement precursors $C_3$, $C_4$ and $C_5$ from their activated fragments. We have found that precipitation of the complement component is complete within about one minute to 2 hours. The complex may be permitted to incubate longer than one hour if necessary, however, no beneficial additional separation of protein is expected to occur beyond one hour. Incubation is carried out at room temperature, that is, about 25° C.

Removal of the precipitate is conveniently accomplished by centrifuging the acridine derivative-protein complex at about 3,000 to 7,000×g for about 10 to 20 minutes then decanting the supernatant which contains the complement fragments $C_{3a}$, $C_{4a}$ and $C_{5a}$ or the des-Arg derivatives thereof. As indicated hereinabove, complement fragments $C_{3a}$, $C_{4a}$ and $C_{5a}$ are rendered inactive in vivo in serum and plasma by carboxypeptidases by conversion to their respective inactive des-Arg derivatives. Such conversion also occurs in vivo in urine. Hence, the supernatant recovered from the novel acridine derivative-precipitation method of the present invention will contain primarily the des-Arg derivative of the complement fragments $C_{3a}$, $C_{4a}$ and $C_{5a}$ rather than the activated form of said fragments when the biological fluid is plasma, serum or urine. For diagnostic purposes measurement of the inactive des-Arg derivative is just as meaningful as the direct measurement of the active form of the complement fragments.

The recovered supernatant is used without further treatment or processing in the immunoassay procedure. We have found that the presence of the acridine derivative in the test samples does not interfere with the antigenicity of the complement fragments or the des-Arg derivatives thereof, thus providing a unique and greatly simplified means of assaying for said fragments.

The immunoassay procedure is not substantially different from known immunoassays for $C_{3a}$, $C_{4a}$ and $C_{5a}$ or the des-Arg derivatives thereof. Equal volumes of the test sample to be assayed, labeled complement fragment $C_{3a}$, $C_{4a}$ or $C_{5a}$ or the des-Arg derivative thereof, and antibody which recognizes said complement fragment are combined and incubated after which the antibody bound and unbound, or free, labeled complement fragment are separated and measured to determine the amount of complement fragment in the test sample by comparison to standard curves. An assay buffer is generally added to the incubate. We have found a buffer comprising HEPES, protamine sulfate, thimerosol and gelatin to be particularly useful.

Purification of the complement fragment $C_3a$, $C_4a$ or $C_5a$ or the des-Arg derivative thereof for use in raising antibody thereto, and for use in generating standard curves as well as for preparing labeled complement fragment can be achieved by the general method described in J. Biol. Chem. 256, 8685-8692 (1981). We have found that this procedure can be modified and improved by substituting the acridine derivative-precipitation technique described hereinabove for the hydrochloric acid precipitation technique.

Antibody to complement fragments $C_3a$, $C_4a$, $C_5a$ or the des-Arg derivatives thereof is raised as generally described by Hugli, et al., J. Biol. Chem. 250, 1472-1478 (1975), and in J. Biol. Chem. 256, 2685-8692 (1981).

The label utilized in the labeled complement fragment or the des-Arg derivative thereof can be any substance capable of detection by physical or chemical means. Radioisotopes such as tritium iodine-131 and iodine-125 are useful with $^{125}I$ being preferred. The $^{125}I$ labeled material can be prepared by various means generally known in the art, such as, the solid-phase lactoperoxidase method. A preferred method employs the use of TCDG (1,3,4,6-tetrachloro-3α,6α-diphenylglycouril) in phosphate buffered saline.

The antibody bound complement fragment can be separated from the free or unbound complement fragment by various means commonly employed in immunoassay procedures. For example, this separation can be achieved by treatment with polyethylene glycol [Desbuquois, B. and Aurback, G. D., J. Clin. Endocrinol. Metab. 33, 732 (1971)] or IgG Sorb or by contacing the incubate with a second antibody. The second antibody, which is prepared by standard procedures, for example, as described in Daughaday, et al., "Principle of Competitive Protein Binding Assay", J. B. Lippincott, Philadelphia (1971), recognizes the complement fragment-antibody complex contained in the incubate. Use of the second antibody technique is particularly preferred.

Standard curves are derived essentially by performing the above-described assay procedure using known quantities of complement fragment $C_3a$, $C_4a$ or $C_5a$ or the des-Arg derivative thereof in place of the test sample. The assay procedure described herein is highly sensitive, and we have found it particularly useful to develop standard curves for concentrations of the complement fragments ranging from 1.0 ng to 25 ng.

The following examples further illustrate the invention. In Examples 3-5 acrinol is used as the precipitating agent and is the preferred acridine derivative of the present invention.

EXAMPLE 1

Purification of complement fragments or the des-Arg derivative

From 2 to 4 liters of serum was activated at 37° C. by addition of boiled yeast (20 mg/ml serum) and allowing the mixture to stand for 45 minutes to one hour. Equal volumes of activated serum and 0.8 to 1.6% acrinol, buffered to pH 7.4 with 0.05M phosphate buffer, were combined and let stand for 30 minutes at 25° C. after which the mixture was centrifuged and the supernatant was decanted. The supernatant was dialyzed against running water overnight at 5°-8° C. then gel filtered on a p-60 column equilibrated with 0.1M ammonium formate, pH 5.0. The fractions containing complement fragments $C_3a$, $C_4a$ or $C_5a$ or the des-Arg derivatives thereof were pooled and applied to an SP-Sephadex column equilibrated with 0.1M ammonium formate, pH 5.0. The column was eluted by a linear gradient of 0.1M to 0.8M ammonium formate, pH 7.0. The fractions of $C_3a$, $C_4a$ and $C_5a$ or the des-Arg derivatives thereof were collected and applied individually to separate CM-cellulose columns and eluted by a gradient of 0.15M to 0.43M ammonium formate, pH 7.0, at a flow rate of 75 ml/hour. Each of the complement components $C_3a$, $C_4a$ or $C_5a$ was pooled with its respective des-Arg derivative recovered from the column and lyophilized then redissolved in water and dialyzed against 1% acetic acid. A final lyophilization and resuspension in water of about 10 mg/ml provided each fragment ready for use.

EXAMPLE 2

$^{125}I$ Complement $C_3a$ or the des-Arg derivative thereof

To an incubation tube was added 50 μg of complement fragment $C_3a$ or the des-Arg derivative thereof, 150 μl of phosphate buffered saline, 100 μg of TCDG and 1 mCi (10 μl) $^{125}I$ sodium. The phosphate buffered saline was prepared as a stock solution comprising 81 mg sodium chloride, 39 mg anhydrous sodium biophosphate, 199 mg sodium phosphate dibasic heptahydrate reagent and 100 ml glass distilled deionized water. The mixture was incubated for 20 minutes at about 25° C. then transferred to a chromatography column equilibrated with phosphate buffered saline with gelatin which was prepared as a stock solution comprising 143 g sodium chloride, 200 mg thimerosol NF, 6 g anhydrous sodium biophosphate, 34 g sodium phosphate dibasic heptahydrate reagent, 17 g gelatin and glass distilled deionized water to a volume of 17.5 liters. Radioactive fractions of 0.5 ml each were collected and diluted to give 20,000 to 60,000 cpm/0.05 ml in phosphate buffered saline with gelatin.

EXAMPLE 3

(a) A mixture of 0.45 ml activated plasma, 0.45 ml of 0.8% acrinol in 0.05M phosphate buffer, pH 7.4, and 0.1 ml distilled water was reacted to about 25° C. for 20 minutes then centrifuged at 1700×g for 10 minutes. The supernatant was collected. A mixture of 50 μl of assay buffer prepared as described hereinabove, 50 μl of supernatant obtained above, 50 μl of $^{125}I$ complement fragment $C_3a$ or the des-Arg derivative thereof and 50 μl of complement fragment $C_3a$ rabbit antisera was incubated for 30 minutes at about 25° C. after which 50 μl of goat anti-rabbit antisera was added and mixed well. The mixture was incubated for an additional 30 minutes at about 25° C. after which 2 ml of isotonic saline was added. The mixture was centrifuged at 2000 g for 10 minutes and the supernatant decanted. The radioactivity of the pellet was 4555 cpm.

(b) The foregoing procedure was performed only the acid-precipitation technique of Hugli and Chenoweth described in Immunoassays: Clinical Laboratory Techniques for the 1980s: 443-460 was substituted for the acrinol precipitation step. The radioactivity of the resultant pellet was 4521-4757 cpm demonstrating that the acrinol precipitation technique removes intact complement protein precursor as effectively as treatment with hydrochloric acid followed by base neutralization providing a greatly improved simplified assay procedure. Also the results of the two experiments indicate that the presence of acrinol does not affect either the first or the second immunological reactions.

In generating standard curves for complement fragment $C_3a$ or the des-Arg derivative thereof using 1.0 ng, 2.5 ng, 5.0 ng, 10 ng, 25 ng and 50 ng quantities of $C_3a$ we found that use of the acrinol precipitation step in place of the acid precipitation-base neutralization step of Hugli and Chenoweth increased the sensitivity of the immunoassay by a factor of 12 as evidenced by the fact that the range of detection became shorter and the slope %B/Bo (Standard Counts/Bound Standard) was increased from −2.3 to −4.0.

EXAMPLE 4

The assay as described in 3(a) above was performed using acivated plasma samples to which known quantities of complement factor $C_3a$ or the des-Arg derivative thereof ranging from 2 to 20 ng was added. The results indicate that there was 100% of the known $C_3a$ concentrations in each of the "spiked" normal samples assayed.

EXAMPLE 5

The essential reagents for the performance of the immunoassay of the present invention are assembled into a mercantile unit as a kit. The kit comprises multiple containers, such as, bottles or other suitable containers as follows:

(a) a first container having therein a buffered solution of 0.8 to 1.6% acrinol;

(b) a second container having therein a labeled reagent selected from $^{125}I$ labeled complement fragments $C_3a$, $C_4a$ or $C_5a$ or the des-Arg derivative thereof;

(c) a third container having therein rabbit antisera to the particular complement fragment;

and which optionally contains the following additional reagents:

(d) a container having therein assay buffer, prepared as described hereinabove;

(e) a container having therein second antibody which binds the product of the initial complement fragment-antibody reaction, preferably goat anti-rabbit antisera;

(f) a container having therein complement fragment standard, 25 ng;

(g) a container having therein complement fragment standard, 10 ng;

(h) a container having therein complement fragment standard, 5 ng;

(i) a container having therein complement fragment standard, 2.5 ng;

(j) a container having therein complement fragment standard, 1.0 ng.

In each of (f) through (j) the complement fragment is either $C_3a$, $C_4a$ or $C_5a$ or the des-Arg derivative thereof depending on which complement fragment is being assayed.

Although the foregoing examples are limited to the separation and assay of complement fragment $C_3a$ or the des-Arg derivative thereof the novel separation and assay procedure of the present invention is equally applicable to complement fragments $C_4a$ and $C_5a$ or the des-Arg derivatives thereof.

We claim:

1. A method for assaying complement fragment $C_3a$, $C_4a$ or $C_5a$ or the des-Arg derivative thereof in a biological sample which comprises combining equal volumes of the biological sample and a solution of 0.8 to 1.6% of an acridine derivative selected from the group consisting of acrinol, acriflavine, acriflavine hydrochloride, and aminacrine, incubating the mixture for about one minute to 2 hours at about 25° C., recovering the supernatant from the resultant precipitate, incubating the supernatant with a known amount of a labeled complement fragment selected from $C_3a$, $C_4a$ or $C_5a$ or the des-Arg derivative thereof and a known amount of antibody which recognizes said complement fragment or des-Arg derivative thereof, separating the free labeled complement fragment from the bound labeled complement fragment, measuring the amount of labeled complement fragment in either the free or antibody bound complement component, and determining the concentration of complement fragment or the des-Arg derivative thereof in the biological sample by comparison to a standard curve.

2. The method of claim 1 wherein the biological sample and the acridine derivative are incubated for about 20 minutes to one hour.

3. The method of claim 1 wherein the solution of the acridine derivative is 2-ethoxy-6,9-diaminoacridine lactate monohydrate buffered with 0.05M phosphate buffer, pH 7.4.

4. The method of claim 3 wherein the label is $^{125}I$.

5. The method of claim 4 wherein the free label complement fragment or des-Arg derivative thereof is separated from the bound labeled complement fragment by the addition of a second antibody.

6. The method of claim 5 wherein complement fragment being assayed is $C_3a$ or the des-Arg derivative thereof.

7. The method of claim 5 wherein the complement fragment being assayed in $C_4a$ or the des-Arg derivative thereof.

8. The method of claim 5 wherein the complement fragment being assayed is $C_5a$ or the des-Arg derivative thereof.

9. A method for removing complement components $C_3$, $C_4$ and $C_5$ from samples of biological fluids and recovering from said fluids complement fragments $C_3a$, $C_4a$ and $C_5a$ or the des-Arg derivatives thereof which comprises combining equal volumes of the biological fluid sample and a buffered solution of 0.8 to 1.6% of an acridine derivative selected from the group consisting of acrinol, acriflavine, acriflavine hydrochloride, and aminacrine, incubating the mixture for about one minute to 2 hours at about 25° C. and recovering the supernatant, containing said complement fragments, from the resultant precipitate.

10. The method of claim 9 wherein the acridine derivaative is 2-ethoxy-6,9-diaminoacridine lactate monohydrate and the buffer is 0.05M phosphate buffer, pH 7.4.

11. The method of claim 9 wherein the mixture is incubated for about 20 minutes to one hour.

12. A mercantile kit wherein the component parts are assembled for use in assaying biological fluids for complement fragments $C_3a$, $C_4a$ or $C_5a$ or the des-Arg derivatives thereof which comprises (a) a first container having therein a buffered solution of 0.8 to 1.6% of an acridine derivative selected from the group consisting of acrinol, acriflavine, acriflavine hydrochloride, and aminacrine;

(b) a second container having therein a labeled reagent selected from labeled complement fragments $C_3a$, $C_4a$ or $C_5a$ or the des-Arg derivatives thereof; and (c) a third container having therein an antibody reagent selected from antibody which recognizes complement fragment $C_3a$, $C_4a$ or $C_5a$ or the des-Arg derivative thereof.

13. The mercantile kit of claim 12 wherein the acridine derivative is 2-ethoxy-6,9-diaminoacridine lactate monohydrate.

14. The mercantile kit of claim 12 which additionally comprises
   (a) a fourth container having therein assay buffer;
   (b) a fifty container having therein a second antibody;
   (c) a sixth container having therein complement fragment $C_3a$, $C_4a$ or $C_5a$ or the des-Arg derivative thereof standard, 25 ng;
   (d) a seventh container having therein complement fragment $C_3a$, $C_4a$ or $C_5a$ or the des-Arg derivative thereof standard, 10 ng;
   (e) an eighth container having therein complement fragment $C_3a$, $C_4a$ or $C_5a$ or the des-Arg derivative thereof standard, 5.0 ng;
   (f) a ninth container having therein complement fragment $C_3a$, $C_4a$ or $C_5a$ or the des-Arg derivative thereof standard, 2.5 ng; and
   (g) a tenth container having therein complement fragment $C_3a$, $C_4a$ or $C_5a$ or the des-Arg derivative thereof standard, 1.0 ng.

15. The mercantile kit of claim 14 wherein the acridine derivative is 2-ethoxy-6,9-diaminoacridine lactate monohydrate.

* * * * *